United States Patent
Feng et al.

(10) Patent No.: US 8,253,122 B2
(45) Date of Patent: Aug. 28, 2012

(54) INFRARED PHYSIOTHERAPEUTIC APPARATUS

(75) Inventors: Chen Feng, Beijing (CN); Kai-Li Jiang, Beijing (CN); Liang Liu, Beijing (CN); Shou-Shan Fan, Beijing (CN)

(73) Assignees: Tsinghua University, Beijing (CN); Hon Hai Precision Industry Co., Ltd., Tu-Cheng, New Taipei (TW)

( * ) Notice: Subject to any disclaimer, the term of this patent is extended or adjusted under 35 U.S.C. 154(b) by 59 days.

(21) Appl. No.: 12/655,509

(22) Filed: Dec. 31, 2009

(65) Prior Publication Data
US 2011/0062350 A1    Mar. 17, 2011

(30) Foreign Application Priority Data

Sep. 11, 2009    (CN) .......................... 2009 1 0190415

(51) Int. Cl.
G01V 5/00    (2006.01)
(52) U.S. Cl. ..................... 250/504 R; 977/742
(58) Field of Classification Search ............... 250/504 R
See application file for complete search history.

(56) References Cited

U.S. PATENT DOCUMENTS

| | | | |
|---|---|---|---|
| 5,698,175 A | 12/1997 | Hiura et al. | |
| 5,788,853 A | 8/1998 | Zenhausern | |
| 5,958,358 A | 9/1999 | Tenne et al. | |
| 6,624,566 B2 * | 9/2003 | Uemura et al. | 313/496 |
| 6,863,942 B2 | 3/2005 | Ren et al. | |
| 6,949,159 B2 * | 9/2005 | Friend et al. | 156/242 |
| 7,077,939 B1 | 7/2006 | Crooks et al. | |
| 7,166,266 B2 | 1/2007 | Nikolaev et al. | |
| 7,212,736 B2 * | 5/2007 | Nelson et al. | 392/412 |
| 7,217,374 B2 * | 5/2007 | Watanabe et al. | 252/502 |
| 7,355,216 B2 | 4/2008 | Yang et al. | |
| 7,569,850 B2 | 8/2009 | Noy et al. | |
| 7,710,649 B2 * | 5/2010 | Feng et al. | 359/489.2 |
| 7,723,684 B1 * | 5/2010 | Haddon et al. | 250/338.1 |
| 7,750,297 B1 | 7/2010 | Chow et al. | |
| 7,814,776 B2 * | 10/2010 | Eklund et al. | 73/24.01 |
| 2003/0185741 A1 | 10/2003 | Matyjaszewski et al. | |
| 2004/0034177 A1 | 2/2004 | Chen | |
| 2004/0043219 A1 * | 3/2004 | Ito et al. | 428/408 |
| 2004/0053780 A1 | 3/2004 | Jiang et al. | |
| 2004/0115114 A1 * | 6/2004 | Gimzewski et al. | 423/445 B |
| 2004/0144970 A1 | 7/2004 | Wang et al. | |

(Continued)

FOREIGN PATENT DOCUMENTS

CN    1066934    12/1992

(Continued)

OTHER PUBLICATIONS

Freitag et al., Mobile Ambipolar Domain in Carbon-Nanotube Infrared Emitters, Aug. 13, 2004, Physical Review Letters, vol. 93, No. 7.*

(Continued)

*Primary Examiner* — Jack Berman
*Assistant Examiner* — Jason McCormack
(74) *Attorney, Agent, or Firm* — Altis Law Group, Inc.

(57) ABSTRACT

An infrared physiotherapeutic apparatus is provided. The infrared physiotherapeutic apparatus includes a supporting element, an infrared radiating element, and a first and second electrode. The infrared radiating element is mounted on the supporting element. The first electrode and the second electrode are spaced apart from each other and electrically connected to the infrared radiating element. The infrared radiating element includes a carbon nanotube structure.

19 Claims, 12 Drawing Sheets

U.S. PATENT DOCUMENTS

| | | | |
|---|---|---|---|
| 2005/0007002 A1 | 1/2005 | Golovchenko et al. | |
| 2005/0208304 A1 | 9/2005 | Collier et al. | |
| 2006/0169975 A1 | 8/2006 | Noy et al. | |
| 2006/0204428 A1 | 9/2006 | Noy et al. | |
| 2006/0275956 A1 | 12/2006 | Konesky | |
| 2007/0128707 A1 | 6/2007 | Rorrer et al. | |
| 2007/0137786 A1 | 6/2007 | Luzzi | |
| 2007/0142559 A1 | 6/2007 | Wang et al. | |
| 2007/0272297 A1* | 11/2007 | Krivoshlykov et al. | 136/256 |
| 2007/0295714 A1 | 12/2007 | Liu et al. | |
| 2008/0039910 A1* | 2/2008 | Chen | 607/100 |
| 2008/0170982 A1* | 7/2008 | Zhang et al. | 423/447.3 |
| 2008/0187648 A1 | 8/2008 | Hart et al. | |
| 2008/0198453 A1* | 8/2008 | LaFontaine et al. | 359/485 |
| 2008/0237464 A1 | 10/2008 | Zhang et al. | |
| 2008/0251274 A1 | 10/2008 | Lee et al. | |
| 2009/0081383 A1* | 3/2009 | Alberding et al. | 427/577 |
| 2009/0085461 A1 | 4/2009 | Feng et al. | |
| 2009/0096348 A1* | 4/2009 | Liu et al. | 313/498 |
| 2009/0296528 A1* | 12/2009 | Jiang et al. | 367/140 |
| 2009/0314765 A1* | 12/2009 | Feng et al. | 219/520 |
| 2010/0017953 A1* | 1/2010 | O'Keeffe et al. | 4/524 |
| 2010/0050619 A1* | 3/2010 | Colvin et al. | 60/311 |
| 2010/0245215 A1* | 9/2010 | Liu et al. | 345/73 |

FOREIGN PATENT DOCUMENTS

| | | |
|---|---|---|
| CN | 2462823 | 12/2001 |
| CN | 101090586 | 12/2007 |
| CN | 101212848 | 7/2008 |
| CN | 101217097 | 7/2008 |
| CN | 101276724 | 10/2008 |
| CN | 101400198 | 4/2009 |
| JP | 2000-195470 | 7/2000 |
| JP | 2005249414 | 9/2005 |
| JP | 2006-147286 | 6/2006 |
| JP | 2006244742 | 9/2006 |
| JP | 2008-198407 | 8/2008 |
| TW | M326535 | 2/2008 |
| TW | I341878 | 7/2009 |
| WO | WO2008118486 | 10/2008 |

OTHER PUBLICATIONS

Xuesong et al., Bottom-up Growth of Carbon Nanotube Multilayers: Unprecedented Grow, Nano Letters (2005), pp. 1997-2000.

Klie et al. Multi-walled carbon nanotubes on amorphous carbon films, Carbon 42 (2004), pp. 1953-1957.

Zhang et al., "Formation of metal nanowires on suspended single-walled carbon nanotubes", Applied physics letters vol. 77, No. 19. Nov. 2000.

Zhu et al., Aligned Carbon Nanotube Stacks by Water-Assisted Selective Etching, Nano Letters, (2005), pp. 2641-2645.

Zhu et al., The growth of carbon nanotube stacks in the kinetics controlled regime, Science Direct, (2006) pp. 344-348.

Zhang et al., "Metal coating on suspended carbon nanotubes and its implication to metal-tube interaction," Chemical physics letters 331 (2000), pp. 35-41.

\* cited by examiner

INFRARED PHYSIOTHERAPEUTIC APPARATUS

RELATED APPLICATIONS

This application claims all benefits accruing under 35 U.S.C. §119 from China Patent Application No. 200910190415.9, filed on Sep. 11, 2009 in the China Intellectual Property Office.

BACKGROUND

1. Technical Field

The present disclosure relates to an infrared physiotherapeutic apparatus based on carbon nanotubes.

2. Description of Related Art

Currently, infrared physiotherapy became an important and popular method for health care and disease treatment.

Referring to FIG. 11, an infrared physiotherapeutic apparatus 10 according to a prior art includes a supporting frame 1, a shell 2, a reflecting plate 3 and a plurality of infrared radiating tubes 4. The supporting frame 1 includes a base (not labeled) and a plurality of flexible metallic tube 11. The base includes an upper device 12 with a controlling circuit 14 therein and a bottom device 13 with a counterweight iron 15 therein. Referring to FIG. 12, the infrared radiating tubes 4 includes a rod-shaped substrate 41, an electro-thermal wire 42 spirally wrapped on a surface of the rod-shaped substrate 41, and an infrared radiating tube 43 configured to accommodate the rod-shaped substrate 4 and the electro-thermal wire 42. The infrared radiating tube 43 can radiate infrared ray after being heated by the electro-thermal wire 42. However, the infrared radiating tube 43 has a relatively low infrared radiating efficiency.

What is needed, therefore, is to provide an infrared physiotherapeutic apparatus which has an improved infrared radiating efficiency.

BRIEF DESCRIPTION OF THE DRAWINGS

Many aspects of the embodiments can be better understood with references to the following drawings. The components in the drawings are not necessarily drawn to scale, the emphasis instead being placed upon clearly illustrating the principles of the embodiments. Moreover, in the drawings, like reference numerals designate corresponding parts throughout several views.

DETAILED DESCRIPTION

The disclosure is illustrated by way of example and not by way of limitation in the figures of the accompanying drawings in which like references indicate similar elements. It should be noted that references to "an" or "one" embodiment in this disclosure are not necessarily to the same embodiment, and such references mean at least one.

Figure 1:
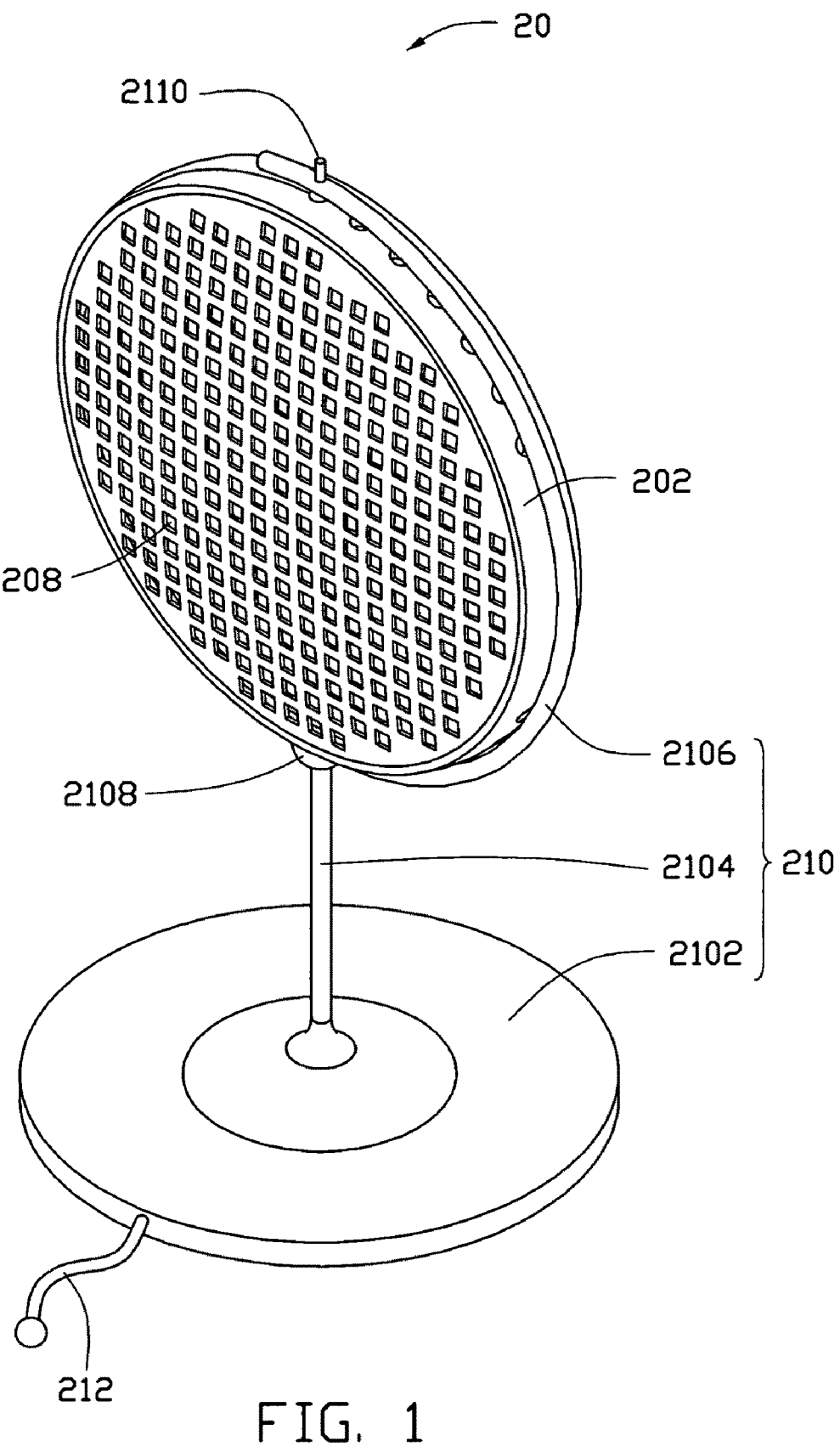
FIG. 1 is a schematic view of one embodiment of an infrared physiotherapeutic apparatus having a carbon nanotube structure.
Figure 2:
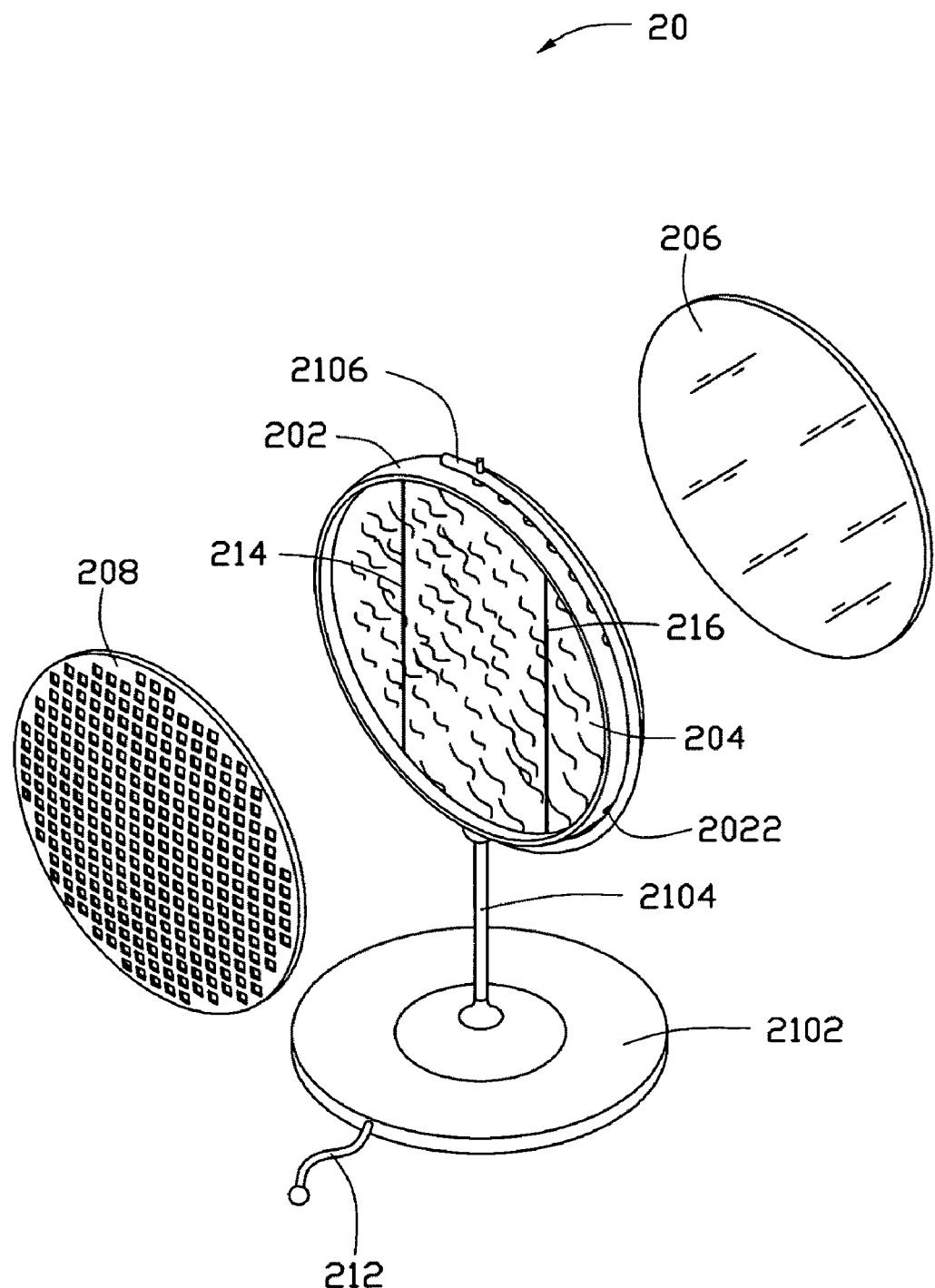
FIG. 2 is an exploded view of the infrared physiotherapeutic apparatus of FIG. 1.

Referring to FIGS. 1 and 2, one embodiment of an infrared physiotherapeutic apparatus 20 includes a bracket 210, a supporting element 202 mounted on the bracket 210, an infrared radiating element 204 mounted on the supporting element 202, a first electrode 214, a second electrode 216, a reflecting element 206 mounted on a first side of the infrared radiating element 204, and a shield 208 mounted on a second side of the infrared radiating element 204.

The bracket 210 is configured to support the supporting element 202. The materials of the bracket 210 can be arbitrary, and can be selected according to need. In one embodiment, the bracket 210 includes a base 2102, a tube 2104 with one end fixed on the base 2102, and a fixing element 2106 connected to the other end of the tube 2104. The base 2102 can be a round metallic box. The tube 2104 is a metal tube with one end fixed on the base 2102, such as by welding. The fixing element 2106 is configured to connect the supporting element 202 to the tube 2104. The shape of the fixing element 2106 can be arbitrary, and can be selected according to need. In one embodiment, the fixing element 2106 is a semicircular-shaped metal rod. Two opposite ends e.g., upper end and lower end of the fixing element 2106, are connected to the supporting element 202 via two pins 2110. The lower end of the fixing element 2106 is connected to a top end of the tube 2104 via a turnable element 2108 such that the supporting element 202 can rotate forward and back around the turnable element 2108. The bracket 210 is optional. In one embodiment, the infrared physiotherapeutic apparatus 20 without the bracket 210 can be hung in front of an object (not shown) which would need to be treated.

The supporting element 202 is connected to the fixing element 2106 via the two pins 2110 such that the supporting element 202 can rotate around the pins 2110. The shape of the supporting element 202 can be arbitrary, and can be selected according to need. The supporting element 202 can be a frame made of insulative materials such as glass, resin, ceramic, wood, quartz or plastic. In one embodiment, the supporting element 202 is a round frame made of heat-resistant resin. A plurality of openings 2022 is defined in the supporting element 202 for heat dissipation.

The first electrode 214 and the second electrode 216 can be fixed on the supporting element 202 and spaced apart from each other. The first electrode 214 and the second electrode 216 can be made of conductive materials such as metal, carbon nanotube or carbon fiber. In one embodiment, the first electrode 214 and the second electrode 216 are two metallic wires. The first electrode 214 and the second electrode 216 are electrically connected to a power cord 212. A switch (not shown) and a controlling circuit (not shown) can be electrically connected between the electrodes 214, 216 and the power cord 212 in series. The leading wires (not shown) between the electrodes 214, 216 and the power cord 212 can be put in the tub 2104 and the base 2102.

The shape and size of the infrared radiating element 204 can correspond to the shape and size of the supporting element 202. The infrared radiating element 204 can be fixed on the inner surface of the supporting element 202, such as by a bolt or heat-resistant adhesive. The infrared radiating element 204 is electrically connected to the first electrode 214 and the second electrode 216.

The infrared radiating element 204 can be a carbon nanotube structure. The carbon nanotube structure includes a plurality of carbon nanotubes uniformly distributed therein. The carbon nanotubes can be joined by van der Waals attractive force therebetween. The carbon nanotube structure can be a substantially pure structure of the carbon nanotubes, with few impurities. The carbon nanotubes can be used to form many different structures and provide a large specific surface area. The heat capacity per unit area of the carbon nanotube structure can be less than $2 \times 10^{-4}$ $J/m^2 *K$. In one embodiment, the heat capacity per unit area of the carbon nanotube structure is less than $1.7 \times 10^{-6}$ $J/m^2 *K$. The infrared radiating element 204 has a high infrared radiating efficiency. If the carbon nanotube structure is substantially pure, the carbon nanotubes will not easily oxidize and the lifespan of the infrared radiating element 204 will be relatively long. Further, the carbon nanotubes have a low density, about 1.35 $g/cm^3$, so the infrared radiating element 204 is light. The infrared radiating element 204 has a high response heating speed because the heat capacity of the carbon nanotube structure is very low, and the temperature of the infrared radiating element 204 can rise and fall quickly. The carbon nanotube structure with a plurality of carbon nanotubes has a large specific surface area because the carbon nanotube has a large specific surface area. If the specific surface of the carbon nanotube structure is large enough, the carbon nanotube structure is adhesive and can be directly applied to a surface.

The carbon nanotubes in the carbon nanotube structure can be arranged orderly or disorderly. A disorderly carbon nanotube structure includes, but is not limited to, a structure where the carbon nanotubes are arranged along many different directions, and the aligning directions of the carbon nanotubes are random. The number of carbon nanotubes arranged along each different direction can be almost the same (e.g. uniformly disordered). The disordered carbon nanotube structure can be isotropic, namely the carbon nanotube film has properties identical in all directions of the carbon nanotube structure. The carbon nanotubes in the disordered carbon nanotube structure can also be entangled with each other.

The carbon nanotube structure including ordered carbon nanotubes is an ordered carbon nanotube structure. An ordered carbon nanotube structure includes, but is not limited to, a structure where the carbon nanotubes are arranged in a consistently systematic manner, e.g., the carbon nanotubes are arranged approximately along a same direction and/or have two or more sections within each of which the carbon nanotubes are arranged approximately along a same direction. Different sections can have different directions. The carbon nanotubes in the carbon nanotube structure can be selected from single-walled, double-walled, or multi-walled carbon nanotubes.

The carbon nanotube structure can be a carbon nanotube film structure with a thickness ranging from about 0.5 nanometer (nm) to about 1 millimeter (mm). The carbon nanotube film structure can include at least one carbon nanotube film. The carbon nanotube structure can also be a linear carbon nanotube structure with a diameter ranging from about 0.5 nm to about 1 mm. The carbon nanotube structure can also be a combination of the carbon nanotube film structure and the linear carbon nanotube structure. It is understood that any carbon nanotube structure described can be used with all embodiments. It is also understood that any carbon nanotube structure may or may not employ the use of a support structure.

Figure 3:
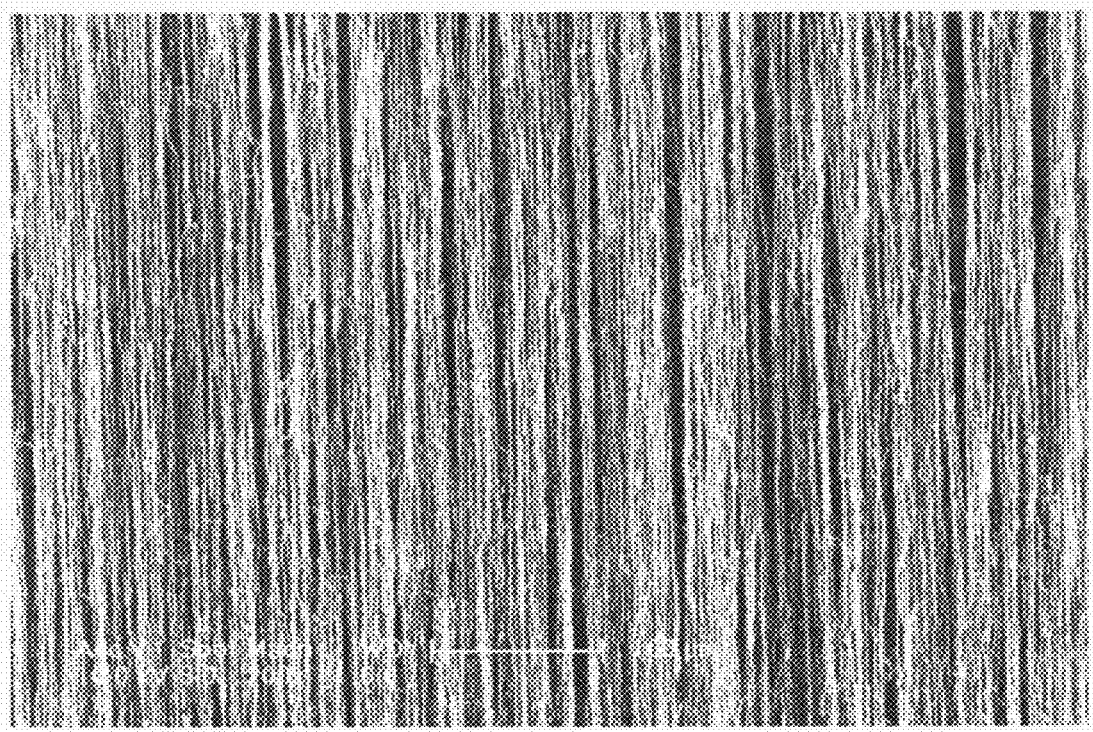
FIG. 3 is a Scanning Electron Microscope (SEM) image of a drawn carbon nanotube film.
Figure 4:
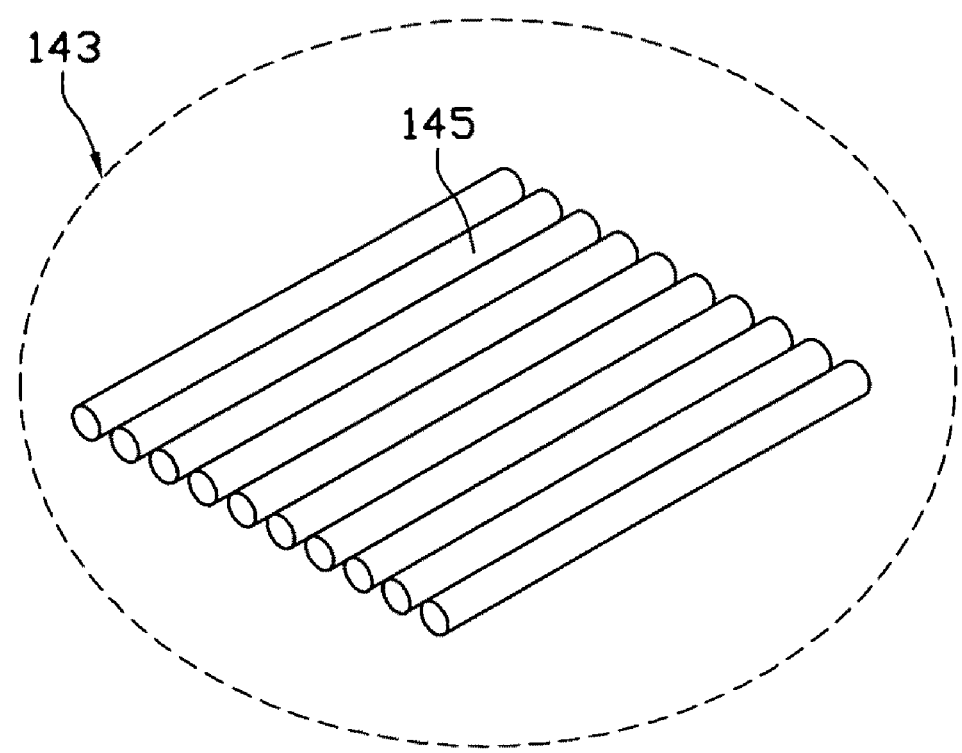
FIG. 4 is a schematic view of a carbon nanotube segment in the drawn carbon nanotube film of FIG. 3.

In one embodiment, the carbon nanotube film structure includes at least one drawn carbon nanotube film. A drawn carbon nanotube film can be drawn from a carbon nanotube array that is able to have a film drawn therefrom. The drawn carbon nanotube film includes a plurality of successive and oriented carbon nanotubes joined end-to-end by van der Waals attractive force therebetween. The drawn carbon nanotube film can be a free-standing film. Referring to FIGS. 3 and 4, each drawn carbon nanotube film includes a plurality of successively oriented carbon nanotube segments 143 joined end-to-end by van der Waals attractive force therebetween. Each carbon nanotube segment 143 includes a plurality of carbon nanotubes 145 substantially parallel to each other, and joined by van der Waals attractive force therebetween. As can be seen in FIG. 3, some variations can occur in the drawn carbon nanotube film. The carbon nanotubes 145 in the drawn carbon nanotube film are substantially oriented along a preferred orientation. The carbon nanotube film can be treated with an organic solvent to increase the mechanical strength and toughness and reduce the coefficient of friction of the carbon nanotube film. A thickness of the carbon nanotube film can range from about 0.5 nm to about 100 micrometers (μm). In one embodiment, the infrared radiating element 204 is the drawn carbon nanotube film. The carbon nanotubes of the infrared radiating element 204 extend from the first electrode 214 to the second electrode 216. The drawn carbon nanotube film can be attached to surfaces of the electrode 214, 214 with an adhesive, by mechanical force, by the adhesive properties of the carbon nanotube film, or by a combination thereof.

The carbon nanotube film structure of the infrared radiating element 204 can include at least two stacked drawn carbon nanotube films. In other embodiments, the carbon nanotube structure can include two or more coplanar carbon nanotube films, and can include layers of coplanar carbon nanotube films. Additionally, when the carbon nanotubes in the carbon nanotube film are substantially aligned along one preferred orientation (e.g., the drawn carbon nanotube film), an angle can exist between the orientation of carbon nanotubes in adjacent films, whether stacked or adjacent. Adjacent carbon nanotube films can only be joined by the van der Waals attractive force therebetween. The number of the layers of the carbon nanotube films is not limited by the length of the carbon nanotube structure. However, the thicker the carbon nanotube structure, the smaller the specific surface area. An angle between the aligned directions of the carbon nanotubes in two adjacent carbon nanotube films can range from about 0 degrees to about 90 degrees. If the angle between the aligned directions of the carbon nanotubes in adjacent stacked carbon nanotube films is larger than 0 degrees, a microporous structure is defined by the carbon nanotubes in the infrared radiating element 204. The carbon nanotube structure in an embodiment employing these films will have a plurality of micropores. Stacking the carbon nanotube films will also add to the structural integrity of the carbon nanotube structure. In some embodiments, the carbon nanotube structure is a free standing structure.

Figure 5:
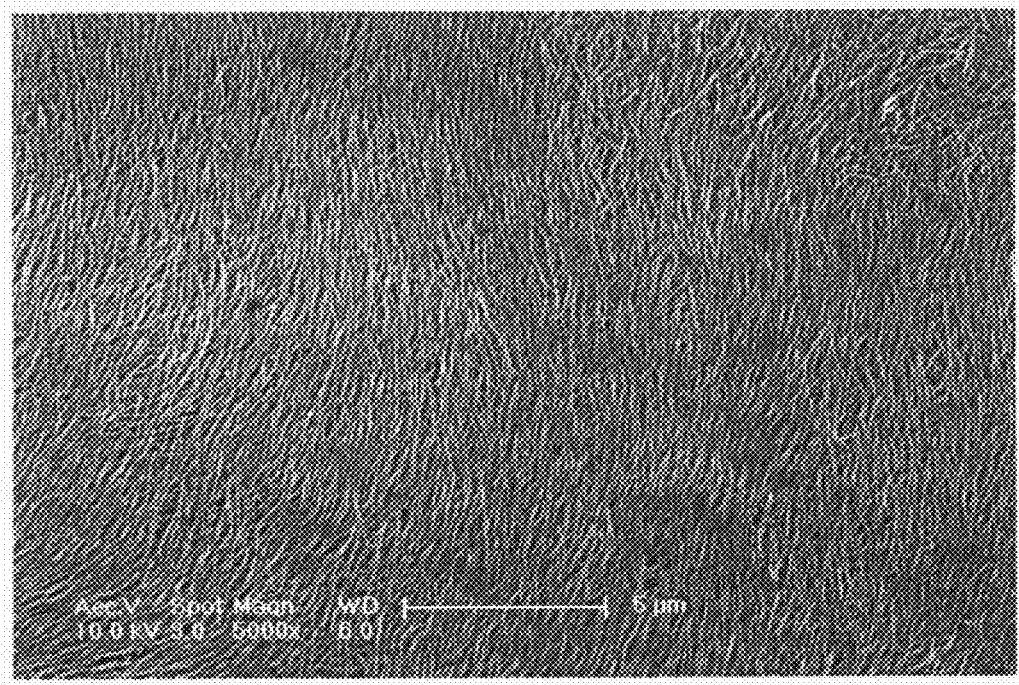
FIG. 5 is an SEM image of a pressed carbon nanotube film.

Referring to FIG. 5, in another embodiment, the carbon nanotube film structure can include at least one pressed carbon nanotube film. The pressed carbon nanotube film can be a free-standing carbon nanotube film. The carbon nanotubes in the pressed carbon nanotube film are arranged along a same direction or arranged along different directions. The carbon nanotubes in the pressed carbon nanotube film can rest upon each other. Adjacent carbon nanotubes are attracted to each other and joined by van der Waals attractive force. An angle between a primary alignment direction of the carbon nanotubes and a surface of the pressed carbon nanotube film is approximately 0 degrees to approximately 15 degrees. The greater the pressure applied, the smaller the angle formed. When the carbon nanotubes in the pressed carbon nanotube film are arranged along different directions, the carbon nanotube structure can be isotropic, and have properties identical in all directions substantially parallel to a surface of the carbon nanotube film. The thickness of the pressed carbon nanotube film ranges from about 0.5 nm to about 1 mm.

Figure 6:
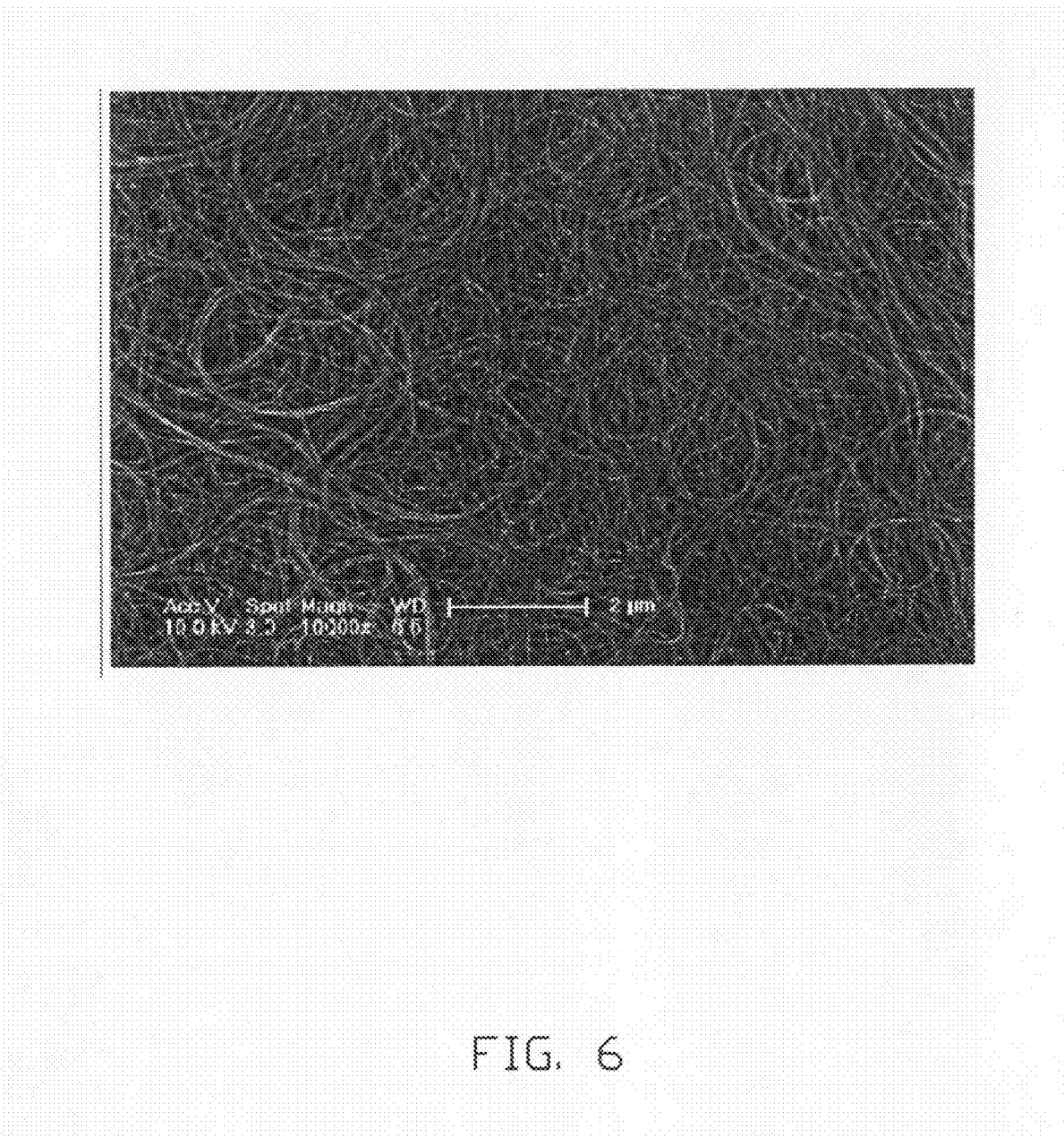
FIG. 6 is an SEM image of a flocculated carbon nanotube film.

Referring to FIG. 6, in another embodiment, the carbon nanotube film structure includes a flocculated carbon nanotube film. The flocculated carbon nanotube film can include a plurality of long, curved, disordered carbon nanotubes entangled with each other. Further, the flocculated carbon nanotube film can be isotropic. The carbon nanotubes can be substantially uniformly dispersed in the carbon nanotube film. Adjacent carbon nanotubes are acted upon by van der Waals attractive force to form an entangled structure with micropores defined therein. It is understood that the flocculated carbon nanotube film is very porous. Sizes of the micropores can be less than 10 micrometers. The porous nature of the flocculated carbon nanotube film will increase the specific surface area of the carbon nanotube structure. Further, because the carbon nanotubes in the carbon nanotube structure are entangled with each other, the carbon nanotube structure employing the flocculated carbon nanotube film has excellent durability, and can be fashioned into desired shapes with a low risk to the integrity of the carbon nanotube structure. The thickness of the flocculated carbon nanotube film can range from about 0.5 nm to about 1 mm.

Carbon nanotube structures can include linear carbon nanotube structures. In other embodiments, the linear carbon nanotube structures, including carbon nanotube wires and/or carbon nanotube cables, can be used.

Figure 7:
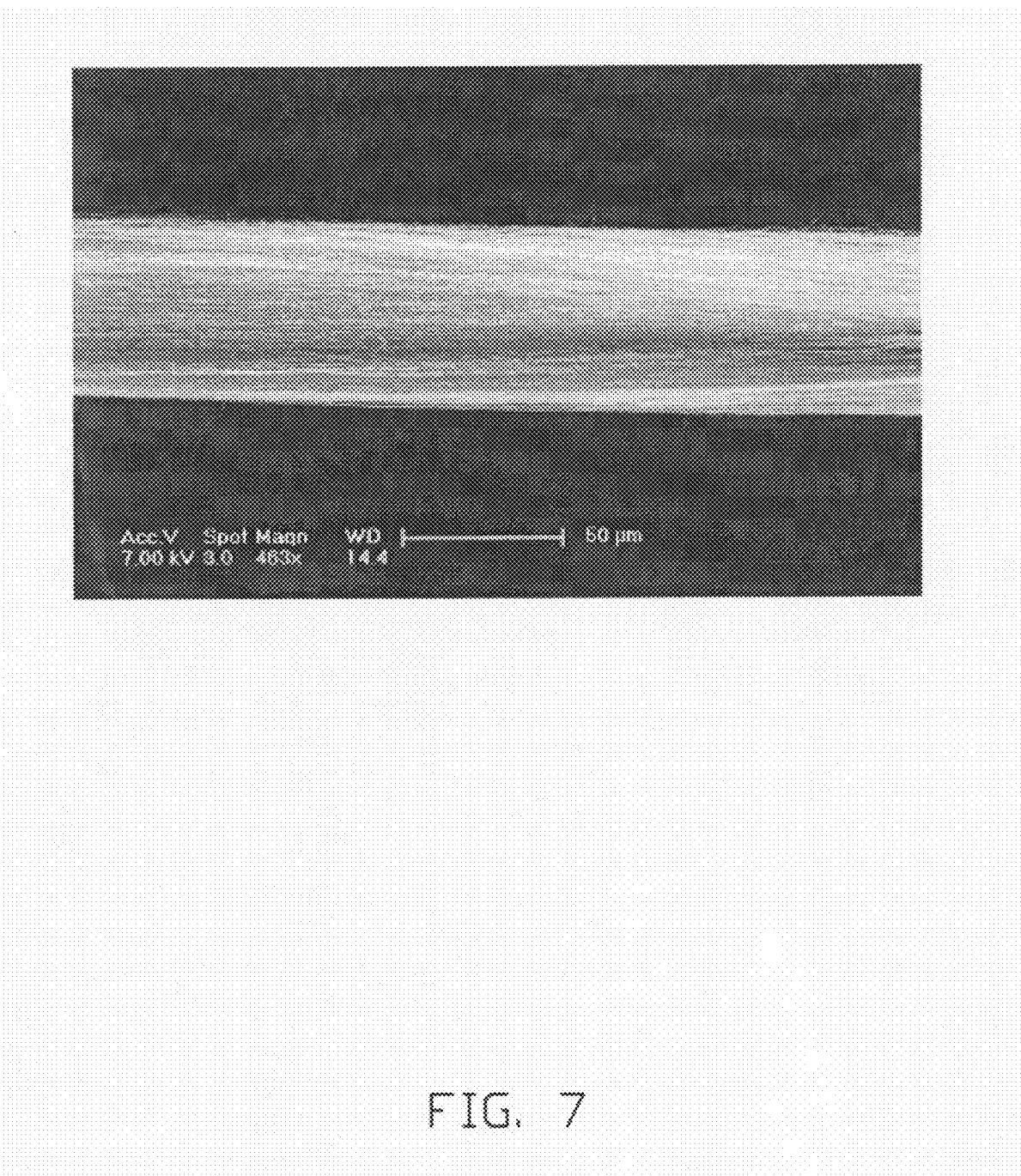
FIG. 7 is an SEM image of an untwisted carbon nanotube wire.

The carbon nanotube wire can be untwisted or twisted. Treating the drawn carbon nanotube film with a volatile organic solvent can form the untwisted carbon nanotube wire. In one embodiment, the organic solvent is applied to soak the entire surface of the drawn carbon nanotube film. During the soaking, adjacent substantially parallel carbon nanotubes in the drawn carbon nanotube film will bundle together, due to the surface tension of the organic solvent as it volatilizes, and thus, the drawn carbon nanotube film will be shrunk into untwisted carbon nanotube wire. Referring to FIG. 7, the untwisted carbon nanotube wire includes a plurality of carbon nanotubes substantially oriented along a same direction (i.e., a direction along the length of the untwisted carbon nanotube wire). The carbon nanotubes are substantially parallel to the axis of the untwisted carbon nanotube wire. More specifically, the untwisted carbon nanotube wire includes a plurality of successive carbon nanotube segments joined end to end by van der Waals attractive force therebetween. Each carbon nanotube segment includes a plurality of carbon nanotubes substantially parallel to each other, and joined by van der Waals attractive force therebetween. The carbon nanotube segments can vary in width, thickness, uniformity, and shape. The length of the untwisted carbon nanotube wire can be arbitrarily set as desired. A diameter of the untwisted carbon nanotube wire ranges from about 0.5 nm to about 100 μm.

Figure 8:
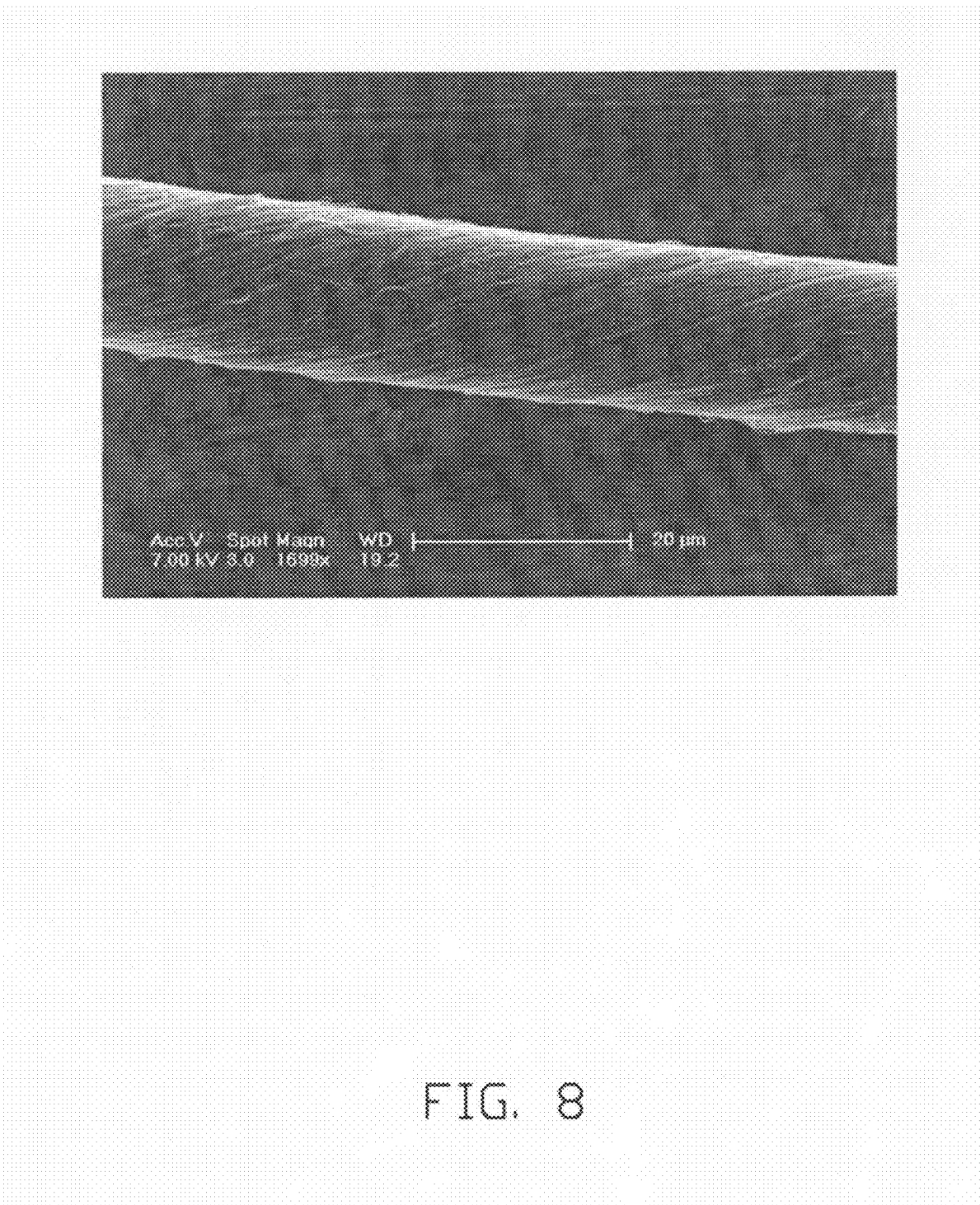
FIG. 8 is an SEM image of a twisted carbon nanotube wire.

The twisted carbon nanotube wire can be formed by twisting a drawn carbon nanotube film using a mechanical force to turn the two ends of the drawn carbon nanotube film in opposite directions. Referring to FIG. 8, the twisted carbon nanotube wire includes a plurality of carbon nanotubes helically oriented around an axial direction of the twisted carbon nanotube wire. More specifically, the twisted carbon nanotube wire includes a plurality of successive carbon nanotube segments joined end to end by van der Waals attractive force therebetween. Each carbon nanotube segment includes a plurality of carbon nanotubes substantially parallel to each other, and joined by van der Waals attractive force therebetween. Length of the carbon nanotube wire can be set as desired. A diameter of the twisted carbon nanotube wire can be from about 0.5 nm to about 100 μm. Further, the twisted carbon nanotube wire can be treated with a volatile organic solvent after being twisted. After being soaked by the organic solvent, the adjacent paralleled carbon nanotubes in the twisted carbon nanotube wire will bundle together, due to the surface tension of the organic solvent when the organic solvent volatilizes. The specific surface area of the twisted carbon nanotube wire will decrease, while the density and strength of the twisted carbon nanotube wire will be increased.

The carbon nanotube cable includes two or more carbon nanotube wires. The carbon nanotube wires in the carbon nanotube cable can be, twisted or untwisted. In an untwisted carbon nanotube cable, the carbon nanotube wires are substantially parallel with each other. In a twisted carbon nanotube cable, the carbon nanotube wires are twisted with each other.

The infrared radiating element 204 can include one or more linear carbon nanotube structures. The plurality of linear carbon nanotube structures can be substantially parallel with each other, crossed with each other, weaved together, or twisted with each other. The resulting structure can be a planar structure if so desired.

In other embodiments, the carbon nanotube structure can include non-carbon nanotube infrared radiating materials such as ceramic, silicon oxide, and/or metal oxide, thus becoming a carbon nanotube composite. The non-carbon nanotube infrared radiating materials can be dispersed in the micropores of the carbon nanotube structure or coated on a surface of the carbon nanotube structure. The infrared radiating efficiency of the infrared radiating element 204 can be further improved by using the carbon nanotube composite.

The shape and size of the reflecting element 206 and shield 208 correspond to the shape and size of the supporting element 202. The reflecting element 206 and shield 208 can be mounted on the supporting element 202 and fixed thereon, for example by a bolt or adhesive. The reflecting element 206 is configured to reflect the infrared ray radiated from the infrared radiating element 204. The reflecting element 206 can be a plate with a surface coated with a reflecting layer. The shield 208 is configured to protect the infrared radiating element 204 and can prevent the user from electric shock. The shield 208 can be a porous structure such as a metallic meshwork or a fabric. The metallic meshwork can be made by etching a metallic plate or weaving metallic wires. In one embodiment, the reflecting element 206 is a round mica plate and the shield 208 is a metallic meshwork. The reflecting element 206 and the shield 208 are mounted on different sides of the radiating element 204.

In use, when a voltage is applied to the first electrode 214 and the second electrode 216, the carbon nanotube structure of the infrared radiating element 204 radiates electromagnetic waves at a certain wavelength. The infrared radiating element 204 has excellent electrical conductivity, thermal stability, and high thermal radiating efficiency because the carbon nanotubes have an ideal black body structure. The infrared radiating element 204 can radiate an electromagnetic wave with a long wavelength when a certain voltage is applied between the first and second electrodes 214, 216. In one embodiment, the infrared radiating element 204 includes about one hundred layers of drawn carbon nanotubes stacked on each other, and the orientation of the carbon nanotubes in two adjacent carbon nanotubes are substantially perpendicular with each other. Each drawn carbon nanotube film has a square shape with an area of about 15 cm². A thickness of the carbon nanotube structure is about 10 µm. When the voltage ranges from about 10 volts to about 30 volts, the temperature of the infrared radiating element 204 ranges from about 50° C. to about 500° C. As an ideal black body structure, the carbon nanotube structure can radiate infrared ray when it reaches a temperature of about 200° C. to about 450° C. The radiating efficiency is relatively high. The percentage of the infrared ray with a wavelength in a range from about 3 µm to about 14 µm of the entire infrared ray is about 80%. The infrared ray with a wavelength in a range from about 3 µm to about 14 µm can be absorbed by the human body effectively, so the infrared physiotherapeutic apparatus 20 having a carbon nanotube structure is an ideal method for health care and disease treatment.

Furthermore, the infrared physiotherapeutic apparatus 20 can be used as a speaker when exposed to air. The carbon nanotube structure can have a large area to cause pressure oscillations in the air by temperature waves generated by the infrared radiating element 204, because the carbon nanotube structure comprises a plurality of carbon nanotubes and has a small heat capacity per unit area. In use, when signals, such as electrical signals, with variations in the signal and/or strength are inputted to the carbon nanotube structure of the infrared radiating element 204, heating is produced in the carbon nanotube structure according to the variations of the signal and/or signal strength. Temperature waves, which are propagated into air, are obtained. The temperature waves produce pressure waves in the air, resulting in sound generation. In this process, the thermal expansion and contraction of the air in the vicinity of the infrared radiating element 204 produces sound. This is distinct from the mechanism of the conventional loudspeaker, in which the pressure waves are created by the mechanical movement of the diaphragm. When the input signals are electrical signals, the operating principle of the infrared radiating element 204 is an "electrical-thermal-sound" conversion. When the input signals are optical signals, the operation principle of the infrared radiating element 204 is an "optical-thermal-sound" conversion. Energy of the optical signals can be absorbed by the infrared radiating element 204 and the resulting energy will then be radiated as heat. This heat causes detectable sound signals due to pressure variation in the air.

Figure 9:
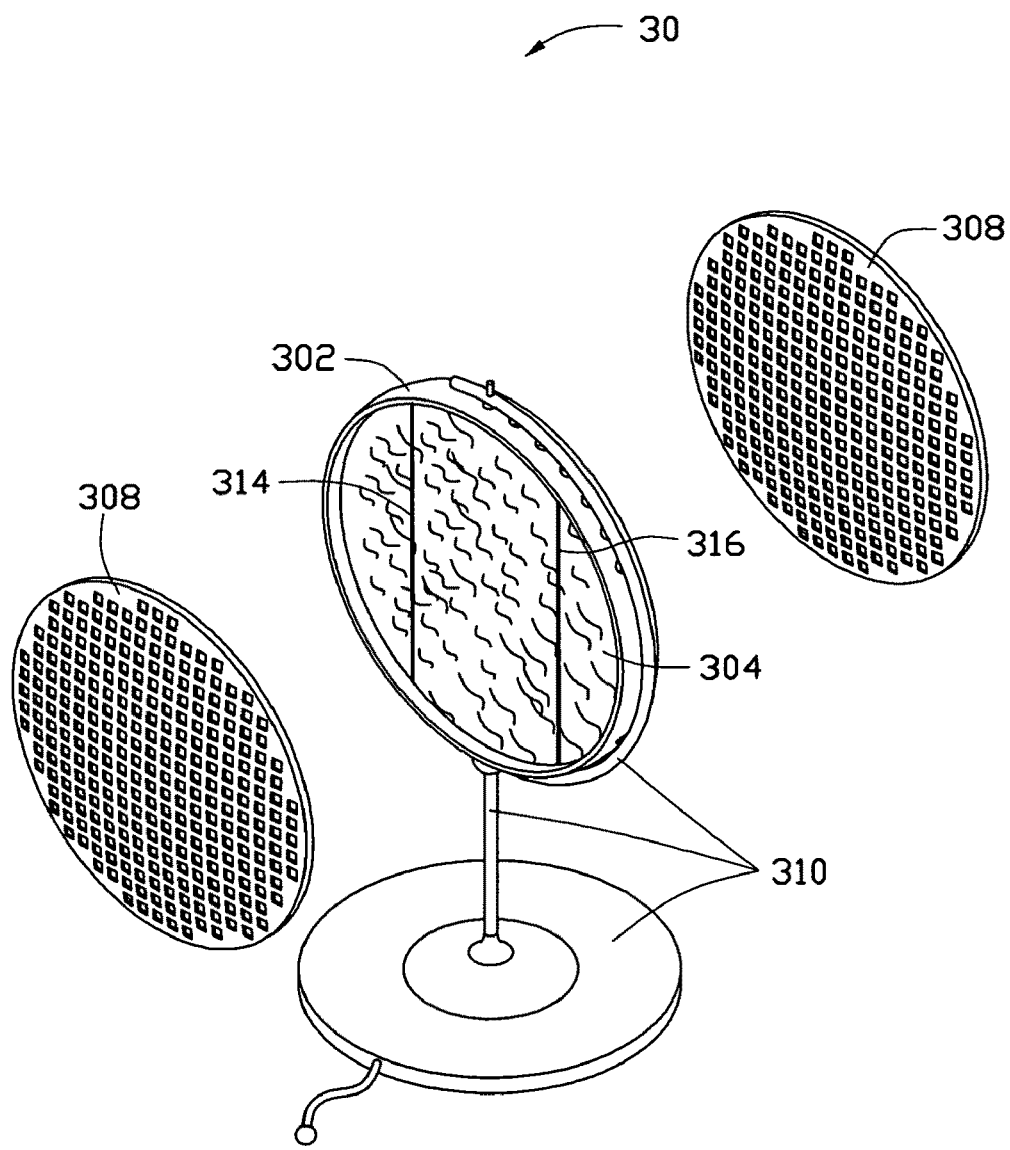
FIG. 9 is an exploded view of another embodiment of an infrared physiotherapeutic apparatus having two shields.

Referring to FIG. 9, another embodiment of an infrared physiotherapeutic apparatus 30 includes a bracket 310, a supporting element 302 mounted on the bracket 310, an infrared radiating element 304 mounted on the supporting element 302, a first electrode 314, a second electrode 316, and two shields 308. The infrared physiotherapeutic apparatus 30 has a structure similar to the infrared physiotherapeutic apparatus 20 described above except that the infrared physiotherapeutic apparatus 30 has two shields 308 mounted on opposite sides of the infrared radiating element 304. The infrared physiotherapeutic apparatus 30 can radiate infrared rays toward opposite directions and allow two persons to get health care and disease treatment simultaneously.

Figure 10:
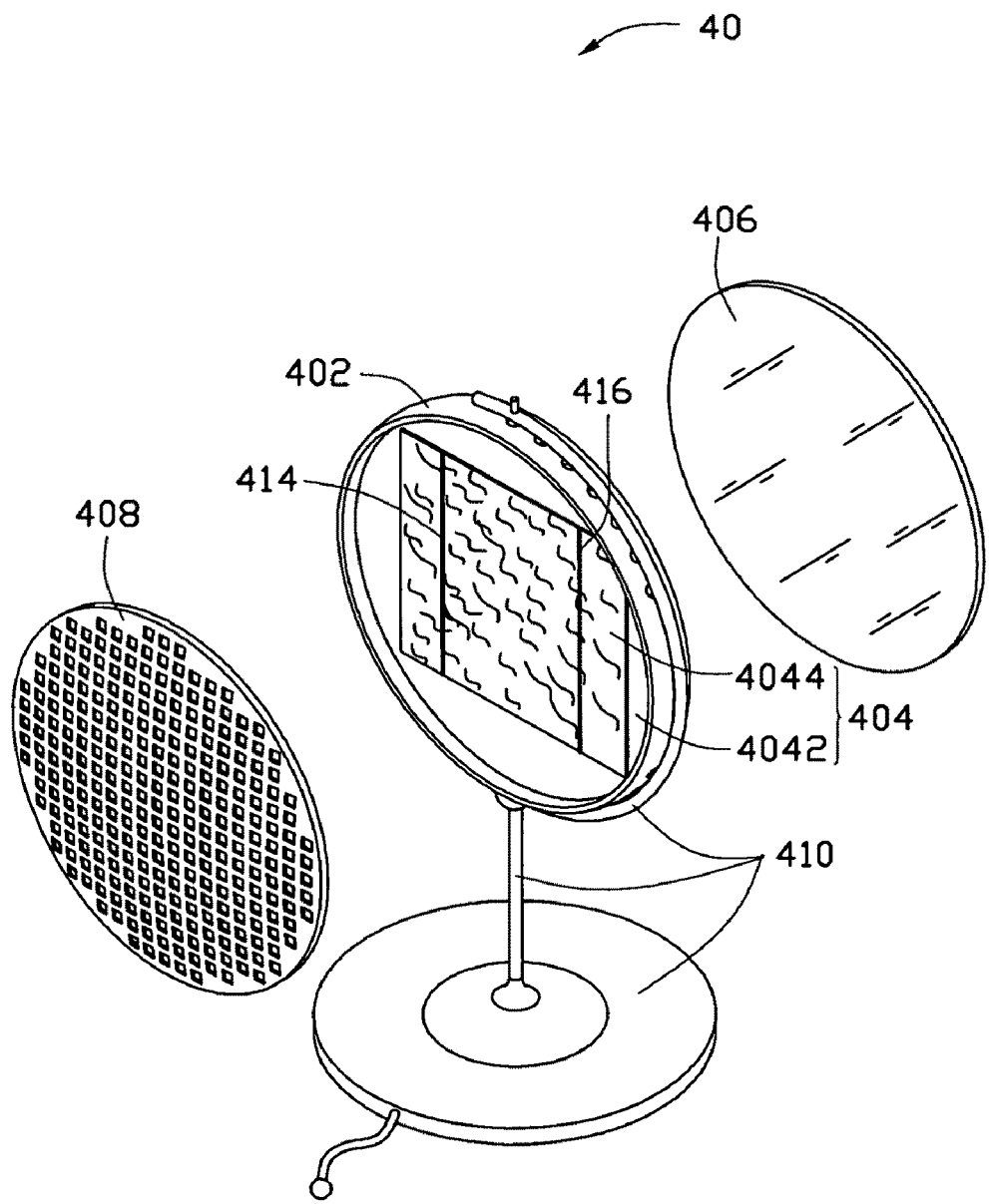
FIG. 10 is an exploded view of another embodiment of an infrared physiotherapeutic apparatus having a carbon nanotube structure on an insulative substrate.
Figure 11:
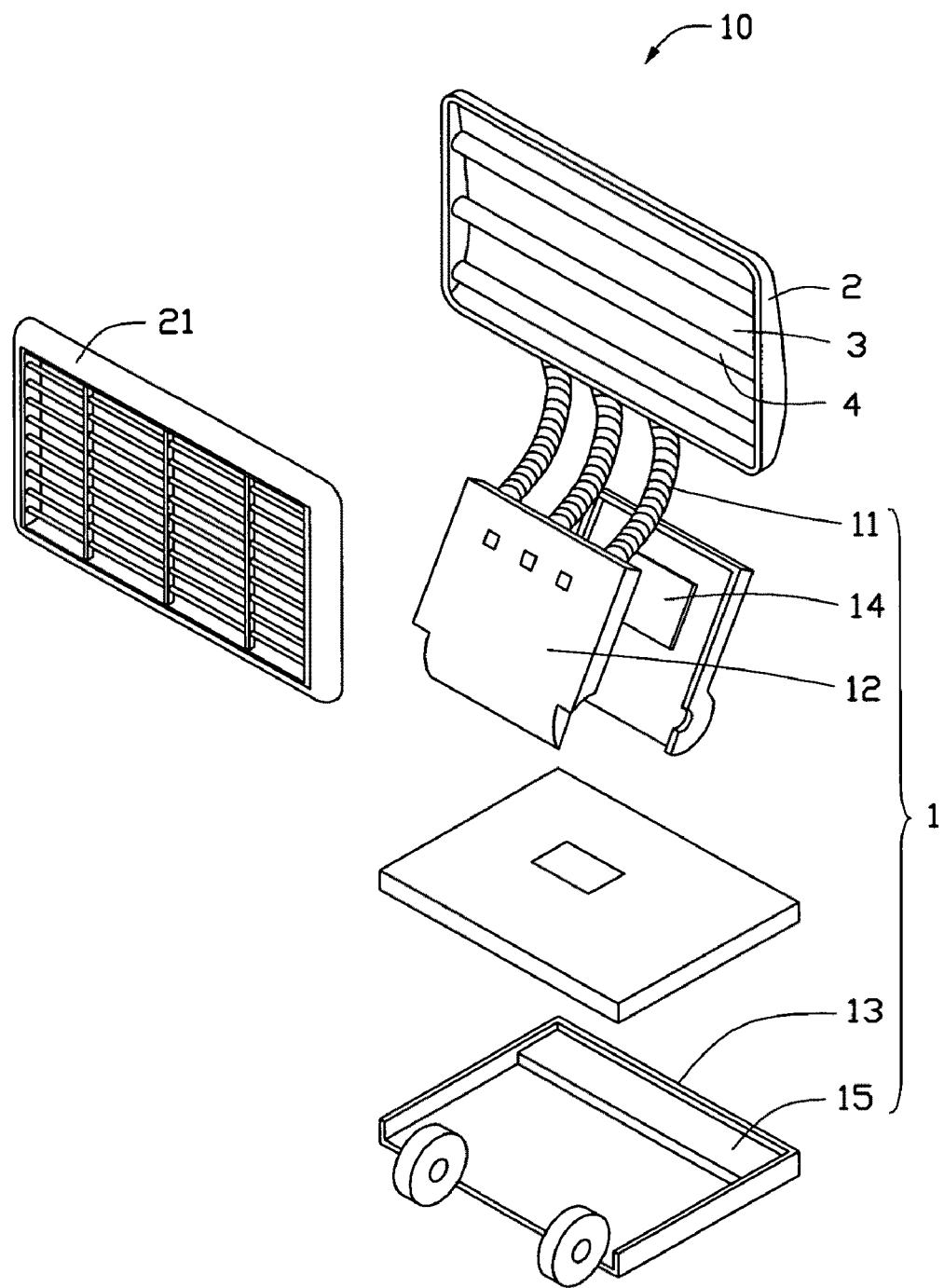
FIG. 11 is a schematic view of an infrared physiotherapeutic apparatus in accordance with the prior art.
Figure 12:
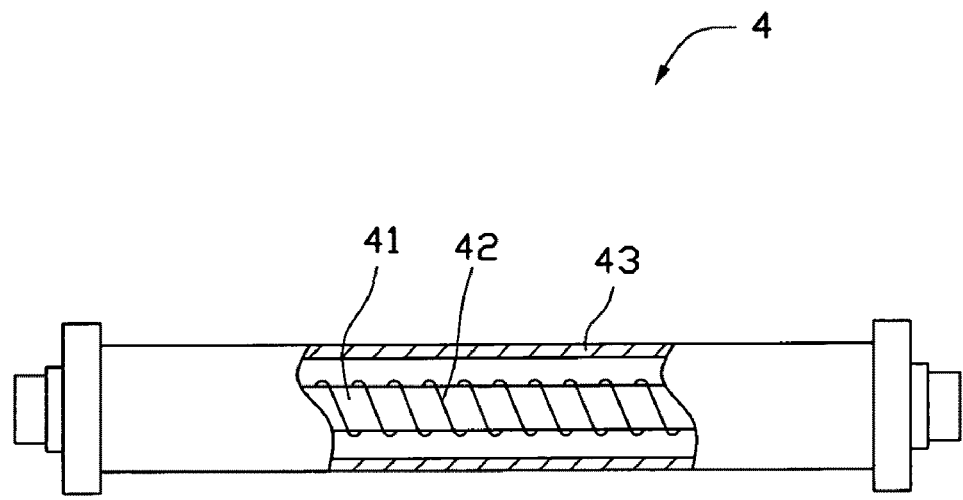
FIG. 12 is a schematic view of an infrared radiating tube of the infrared physiotherapeutic apparatus of FIG. 11.

Referring to FIG. 10, an infrared physiotherapeutic apparatus 40 of another embodiment is shown. The infrared physiotherapeutic apparatus 40 includes a bracket 410, a supporting element 402 mounted on the bracket 410, an infrared radiating element 404 mounted on the supporting element 402, a first electrode 414, a second electrode 416, a reflecting element 406 mounted on one side of the infrared radiating element 404, and a shield 408 mounted on the other side of the infrared radiating element 404. The infrared physiotherapeutic apparatus 40 has a structure similar to the infrared physiotherapeutic apparatus 20 described above except that the infrared radiating element 404 includes an insulative substrate 4042 and a carbon nanotube structure 4044 located on a surface of the insulative substrate 4042. The first electrode 414 and the second electrode 416 are located on the insulative substrate 4042 and spaced from each other. In one embodiment, the insulative substrate 4042 is a round ceramic plate and the carbon nanotube structure 4044 is located on a surface of the insulative substrate 4042 opposite to the shield 408. The carbon nanotube structure 4044 can be the free standing carbon nanotube structure described above or a non-free standing carbon nanotube structure formed on the insulative substrate 4042 by for example, screen printing.

When the free standing carbon nanotube structure is supported by the electrodes 414, 416 such that at least part of the carbon nanotube structure is exposed to air, the infrared physiotherapeutic apparatus 40 can be used as a speaker.

In another embodiment, the infrared radiating element 404 can include an insulative substrate 4042, a carbon nanotube structure 4044, and an infrared radiating layer (not shown) located on opposite surfaces of the insulative substrate 4042 respectively. The infrared radiating layer can be made of materials such as carbon nanotube, ceramic, silicon oxide, and/or metal oxide. The reflecting element 406 can be replaced by another shield similar to the shield 408.

It is to be understood that the above-described embodiments are intended to illustrate rather than limit the disclosure. Variations may be made to the embodiments without departing from the spirit of the disclosure as claimed. The above-described embodiments illustrate the disclosure but do not restrict the scope of the disclosure.

What is claimed is:

1. An infrared physiotherapeutic apparatus comprising:
a supporting element;
an infrared radiating element mounted on the supporting element, the infrared radiating element comprising a carbon nanotube structure configured to convert electric energy to infrared ray and an insulative substrate, wherein the carbon nanotube structure is located on a surface of the insulative substrate; and
a first electrode and a second electrode, the first electrode and the second electrode being spaced apart from each other and electrically connected to the infrared radiating element.

2. The infrared physiotherapeutic apparatus of claim 1, wherein a heat capacity per unit area of the carbon nanotube structure is less than $2 \times 10^{-4}$ J/m²*K.

3. The infrared physiotherapeutic apparatus of claim 1, wherein the carbon nanotube structure is a free standing structure.

4. The infrared physiotherapeutic apparatus of claim 1, wherein the carbon nanotube structure comprises a carbon nanotube film structure, the carbon nanotube film structure comprising a plurality of carbon nanotubes substantially oriented along a same direction extending from the first electrode to the second electrode.

5. The infrared physiotherapeutic apparatus of claim 4, wherein the carbon nanotubes of the carbon nanotube film structure are joined end-to-end by Van der Waals attractive force therebetween.

6. The infrared physiotherapeutic apparatus of claim 1, wherein the carbon nanotube structure comprises a carbon nanotube film structure, the carbon nanotube film structure comprising a plurality of carbon nanotubes entangled with each other.

7. The infrared physiotherapeutic apparatus of claim 1, wherein the carbon nanotube structure comprises a carbon nanotube film structure, the carbon nanotube film structure comprising a plurality of carbon nanotubes resting upon each other; an angle between an alignment direction of the carbon nanotubes and a surface of the carbon nanotube film structure ranges from about 0 degrees to about 15 degrees.

8. The infrared physiotherapeutic apparatus of claim 1, wherein the carbon nanotube structure comprises at least one untwisted carbon nanotube wire, the at least one untwisted carbon nanotube wire comprising a plurality of carbon nanotubes substantially oriented along a direction of an axis of the untwisted carbon nanotube wire.

9. The infrared physiotherapeutic apparatus of claim 1, wherein the carbon nanotube structure comprises at least one twisted carbon nanotube wire, the at least one twisted carbon nanotube wire comprising a plurality of carbon nanotubes helically oriented around an axis of the twisted carbon nanotube wire.

10. The infrared physiotherapeutic apparatus of claim 1, wherein the infrared radiating element further comprises non-carbon nanotube infrared radiating materials selected from the group consisting of ceramic, silicon oxide, and metal oxide.

11. The infrared physiotherapeutic apparatus of claim 10, wherein the carbon nanotube structure defines a plurality of micropores and the non-carbon nanotube infrared radiating materials are dispersed in the micropores of the carbon nanotube structure.

12. The infrared physiotherapeutic apparatus of claim 10, wherein the infrared radiating materials are coated on a surface of the carbon nanotube structure.

13. The infrared physiotherapeutic apparatus of claim 1, wherein the carbon nanotube structure is a non-free standing carbon nanotube structure and formed on the insulative substrate by screen printing.

14. The infrared physiotherapeutic apparatus of claim 1, further comprising a reflecting element and a shield mounted on opposite sides of the infrared radiating element.

15. The infrared physiotherapeutic apparatus of claim 1, further comprising a bracket supporting the supporting element, the bracket comprising a base, a tube having a first end fixed on the base, and a fixing element mounting the supporting element, wherein the fixing element is connected to a second end of the tube and rotatable around the tube.

16. The infrared physiotherapeutic apparatus of claim 15, wherein the supporting element is connected to the fixing element and rotatable around the fixing element.

17. An infrared physiotherapeutic apparatus comprising:
a supporting casing;
a free-standing carbon nanotube structure having a planar configuration and received in the supporting casing, wherein at least part of the carbon nanotube structure is suspended in air and configured to convert electric energy to infrared ray and produce a sound; and
a first electrode and a second electrode, the first electrode and the second electrode being spaced apart from each other and electrically connected to the carbon nanotube structure.

18. The infrared physiotherapeutic apparatus of claim 17, further comprising a shield attached on a side of the carbon nanotube structure, and a reflecting element attached on another side of the carbon nanotube structure.

19. An infrared physiotherapeutic apparatus comprising:
a bracket;
a supporting element mounted on the bracket;
an infrared radiating element mounted on the supporting element, the infrared radiating element comprising a carbon nanotube structure configured to convert electric energy to infrared ray;
a reflecting element mounted on one side of the infrared radiating element; and
a shield mounted on another side of the infrared radiating element; and
a first electrode and a second electrode, the first electrode and the second electrode being spaced apart from each other and electrically connected to the infrared radiating element.

* * * * *